United States Patent [19]

Stocklin

[11] Patent Number: 4,858,612

[45] Date of Patent: Aug. 22, 1989

[54] HEARING DEVICE

[76] Inventor: Philip L. Stocklin, P.O. Box 2111, Satellite Beach, Fla. 32937

[21] Appl. No.: 562,742

[22] Filed: Dec. 19, 1983

[51] Int. Cl.$^4$ ............................................. A61N 1/36
[52] U.S. Cl. ............................... 128/422; 178/419 S
[58] Field of Search ................ 128/419 R, 419 S, 422, 128/653, 771, 732, 741, 746, 791, 804; 340/407

[56] References Cited

U.S. PATENT DOCUMENTS

| | | | |
|---|---|---|---|
| 3,490,458 | 1/1970 | Allison | 128/421 |
| 3,751,605 | 8/1973 | Michelson | 128/1 R |
| 3,951,134 | 4/1976 | Malech | 128/131 |
| 4,428,377 | 1/1984 | Zollner et al. | 128/419 R |

FOREIGN PATENT DOCUMENTS

| | | | |
|---|---|---|---|
| 893311 | 2/1972 | Canada | 128/422 |
| 2811120 | 9/1978 | Fed. Rep. of Germany | 128/419 R |
| 591196 | 1/1978 | U.S.S.R. | 128/419 R |

OTHER PUBLICATIONS

Gerkin, G., "Electroencephalography & Clinical Neurophysiology", vol. 135, No. 6, Dec. 1973, pp. 652–653.
Frye et al., "Science", vol. 181, Jul. 27, 1973, pp. 356–358.
Bise, William, "Low Power Radio-Frequency and Microwave Effects on Human Electroencephalogram and Behavior", Physiol. Chem. & Physics 10 (1978).

Primary Examiner—William E. Kamm
Attorney, Agent, or Firm—Wegner & Bretschneider

[57] ABSTRACT

A method and apparatus for simulation of hearing in mammals by introduction of a plurality of microwaves into the region of the auditory cortex is shown and described. A microphone is used to transform sound signals into electrical signals which are in turn analyzed and processed to provide controls for generating a plurality of microwave signals at different frequencies. The multifrequency microwaves are then applied to the brain in the region of the auditory cortex. By this method sounds are perceived by the mammal which are representative of the original sound received by the microphone.

29 Claims, 7 Drawing Sheets

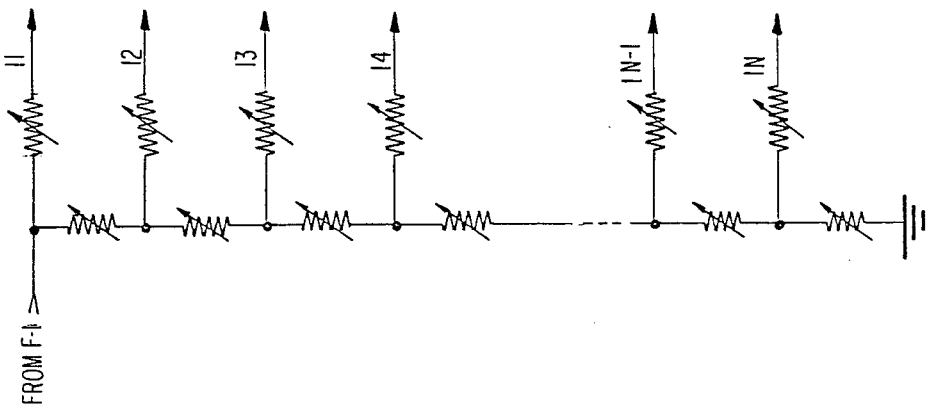
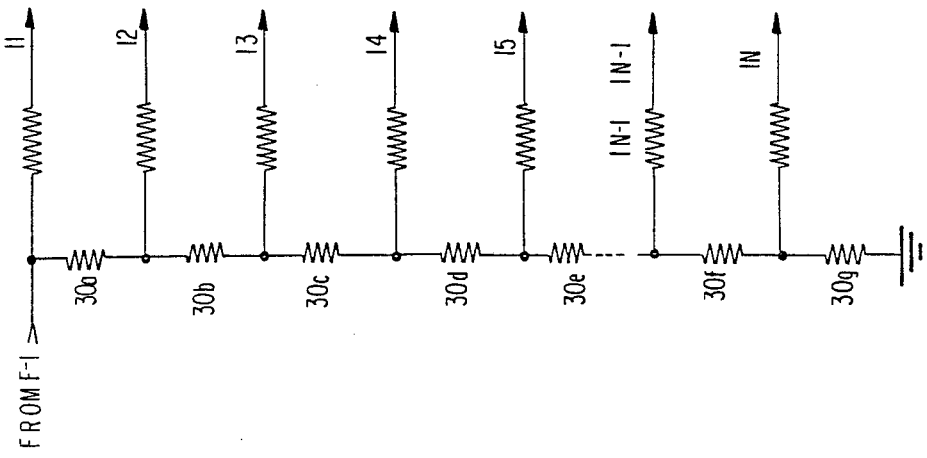
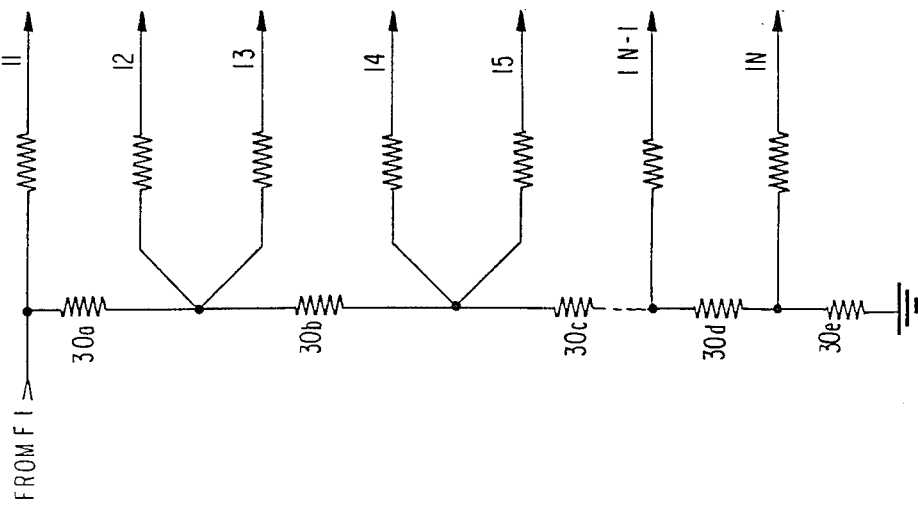

$\xi, r,$ AND $\phi$ RELATED TO CARTESIAN COORDINATES $x, y, z$

SECTION A-A

TRANSFORMATION EQUATIONS $$x = a(\xi^2 - 1)^{1/2} (1-r^2)^{1/2} \cos\phi$$

$$y = -a(\xi^2 - 1)^{1/2} (1-r^2)^{1/2} \sin\phi$$

$$z = a\xi r$$

$1 \leq \xi \leq$ $-1 \leq \phi \leq +1$ $0 \leq \phi \leq 2\pi$

TRANSVERSE ELECTRIC MODES

PRIMARY AUDITORY CORTEX

4,858,612

HEARING DEVICE

BACKGROUND OF THE INVENTION

1. Field of the Invention

This invention relates to devices for aiding of hearing in mammals. The invention is based upon the perception of sounds which is experienced in the brain when the brain is subjected to certain microwave radiation signals.

2. Description of the Prior Art

In prior art hearing devices for human beings, it is well known to amplify sounds to be heard and to apply the amplified sound signal to the ear of the person wearing the hearing aid. Hearing devices of this type are however limited to hearing disfunctions where there is no damage to the auditory nerve or to the auditory cortex. In the prior art, if there is damage to the auditory cortex or the auditory nerve, it cannot be corrected by the use of a hearing aid.

During World War II, individuals in the radiation path of certain radar installations observed clicks and buzzing sounds in response to the microwave radiation. It was through this early observation that it became known to the art that microwaves could cause a direct perception of sound within a human brain. These buzzing or clicking sounds however were not meaningful, and were not perception of sounds which could otherwise be heard by the receiver. This type of microwave radiation was not representative of any intelligible sound to be perceived. In such radar installations, there was never a sound which was generated which resulted in subsequent generation of microwave signals representative of that sound.

Since the early perception of buzzing and clicking, further research has been conducted into the microwave reaction of the brain. In an article entitled "Possible Microwave Mechanisms of the Mammalian Nervous System" by Philip L. Stocklin and Brain F. Stocklin, published in the TIT Journal of Life Sciences, Tower International Technomedical Institute, Inc. P.O. Box 4594, Philadelphia, Pa. (1979) there is disclosed a hypothesis that the mammalian brain generates and uses electro magnetic waves in the lower microwave frequency region as an integral part of the functioning of the central and peripheral nervous systems. This analysis is based primarily upon the potential energy of a protein integral in the neural membrane.

In an article by W. Bise entitled "Low Power Radio-Frequency and Microwave Effects On Human Electro-encephalogram and Behavior", Physiol. Chemistry Phys. 10, 387 (1978), it is reported that there are significant effects upon the alert human EEG during radiation by low intensity CW microwave electromagnetic energy. Bise observed significant repeatable EEG effects for a subject during radiation at specific microwave frequencies.

SUMMARY OF THE INVENTION

Results of theoretical analysis of the physics of brain tissue and the brain/skull cavity, combined with experimentally-determined electromagnetic properties of mammalian brain tissue, indicate the physical necessity for the existence of electromagnetic standing waves, called modes in the living mammalian brain. The mode characteristics may be determined by two geometric properties of the brain; these are the cephalic index of the brain (its shape in prolate spheroidal coordinates) and the semifocal distance of the brain (a measure of its size). It was concluded that estimation of brain cephalic index and semifocal distance using external skull measurements on subjects permits estimation of the subject's characteristic mode frequencies, which in turn will permit a mode by mode treatment of the data to simulate hearing.

This invention provides for sound perception by individuals who have impaired hearing resulting from ear damage, auditory nerve damage, and damage to the auditory cortex. This invention provides for simulation of microwave radiation which is normally produced by the auditory cortex. The simulated brain waves are introduced into the region of the auditory cortex and provide for perceived sounds on the part of the subject.

BRIEF DESCRIPTION OF THE DRAWINGS

FIG. 3 shows a typical voltage divider network which may be used to provide mode partition.

FIG. 4 shows another voltage divider device which may be used to provide mode partition.

FIG. 5 shows a voltage divider to be used as a mode partition wherein each of the resistors is variable in order to provide adjustment of the voltage outputs.

DETAILED DESCRIPTION OF THE PREFERRED EMBODIMENT

Figure 1:
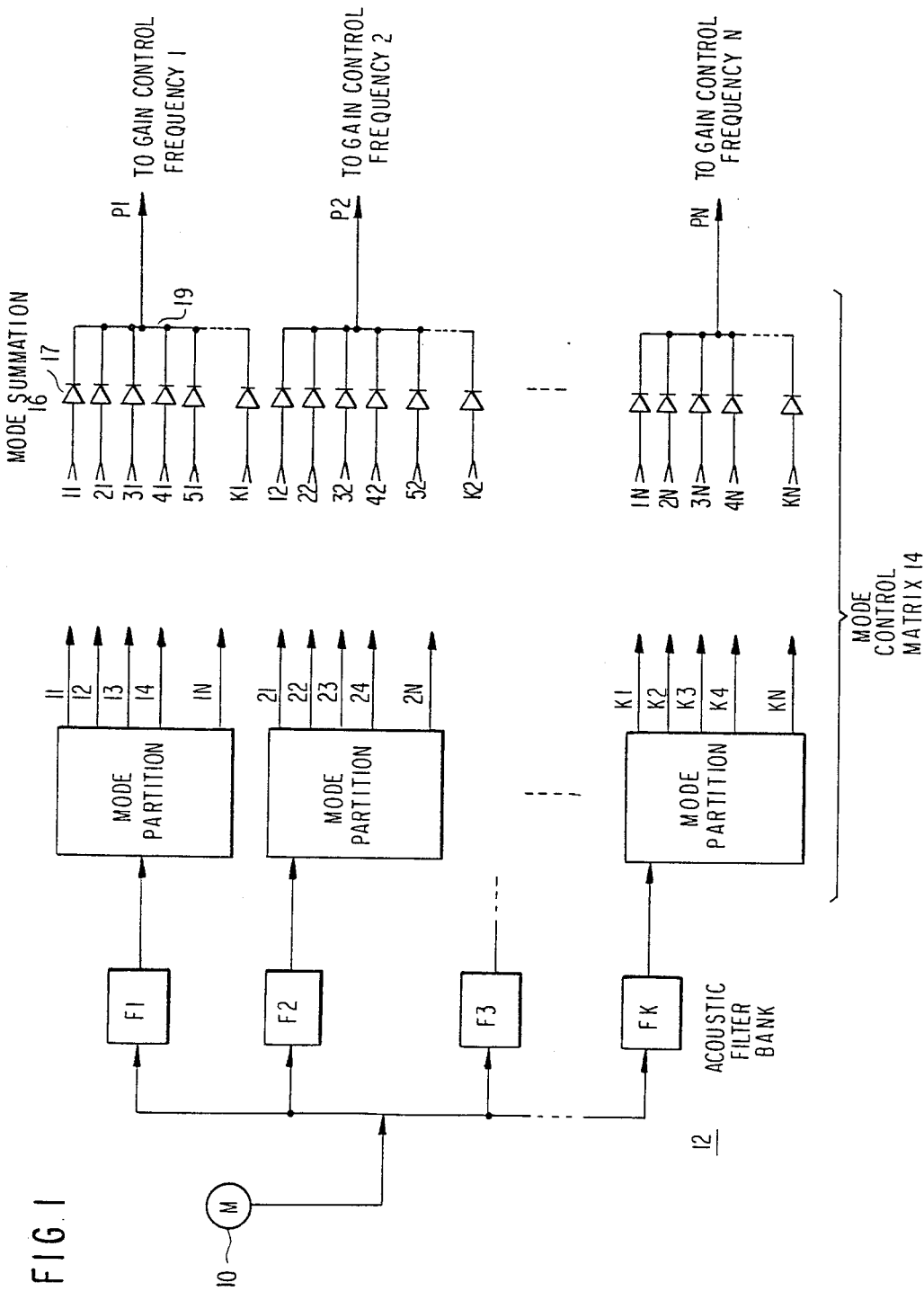
FIG. 1 shows the acoustic filter bank and mode control matrix portions of the hearing device of this invention.

This invention is based upon observations of the physical mechanism the mammalian brain uses to perceive acoustic vibrations. This observation is based in part upon neuro anatomical and other experimental evidence which relates to microwave brain stimulation and the perception of sounds.

It is has been observed that monochromatic acoustic stimuli (acoustic tones, or single tones) of different frequencies uniquely stimulate different regions of the cochlea. It has also been observed that there is a corresponding one to one relationship between the frequency of a monochromatic acoustic stimulus and the region of the auditory cortex neurally stimulated by the cochlear nerve under the physiologically normal conditions (tonotopicity).

It is has been observed that for an acoustic tone of a frequency which is at the lower end of the entire acoustical range perceivable by a person, that a thin lateral region ("Line") parallel to the medial axis of the brain and toward the inferior portion of the primary auditory cortex is stimulated. For an acoustic tone whose frequency is toward the high end of the entire perceivable acoustic range, a thin lateral region parallel to the medial axis and toward the superior portion of the primary auditory cortex is stimulated.

Neural stimulation results in the generation of a broad band of microwave photons by the change in rotational energy state of protons integral to the neuron membrane of the auditory cortex. The physical size and shape of the brain/skull cavity, together with the (semiconductor) properties (conductivity and dielectric constant) of the brain tissue provide an electromagnetic resonant cavity. Specific single frequencies are constructively reinforced so that a number of standing electromagnetic waves, each at its own single electromagnetic frequency in the microwave frequency region, are generated in the brain. Each such standing electromagnetic wave is called a characteristic mode of the brain/skull cavity.

Analysis in terms of prolate spheroidal wave functions indicates that transverse electric field components of these modes have maxima in the region of the auditory cortex. This analysis further shows that transverse electric field possess a variation of amplitude with angle in the angular plane (along the vertical dimension of the auditory cortex) and that is dependent only upon the primary mode number.

The auditory cortex in the normally functioning mammalian brain is a source of microwave modes. The auditory cortex generates these modes in accordance with the neural stimulation of the auditory cortex by the cochlear nerve. Mode weighting for any one acoustic tone stimulus is given by the amplitude of each mode along the line region of the auditory cortex which is neurally stimulated by that acoustic tone stimulus. A listing of mode weighting versus frequency of acoustic stimulus is called the mode matrix.

In this invention, the functions of the ear, the cochlear nerve, and the auditory cortex are simulated. Microwaves simulating the mode matrix are inserted directly into the region of the auditory cortex. By this insertion of simulated microwave modes, the normal operation of the entire natural hearing mechanism is simulated.

Figure 2:
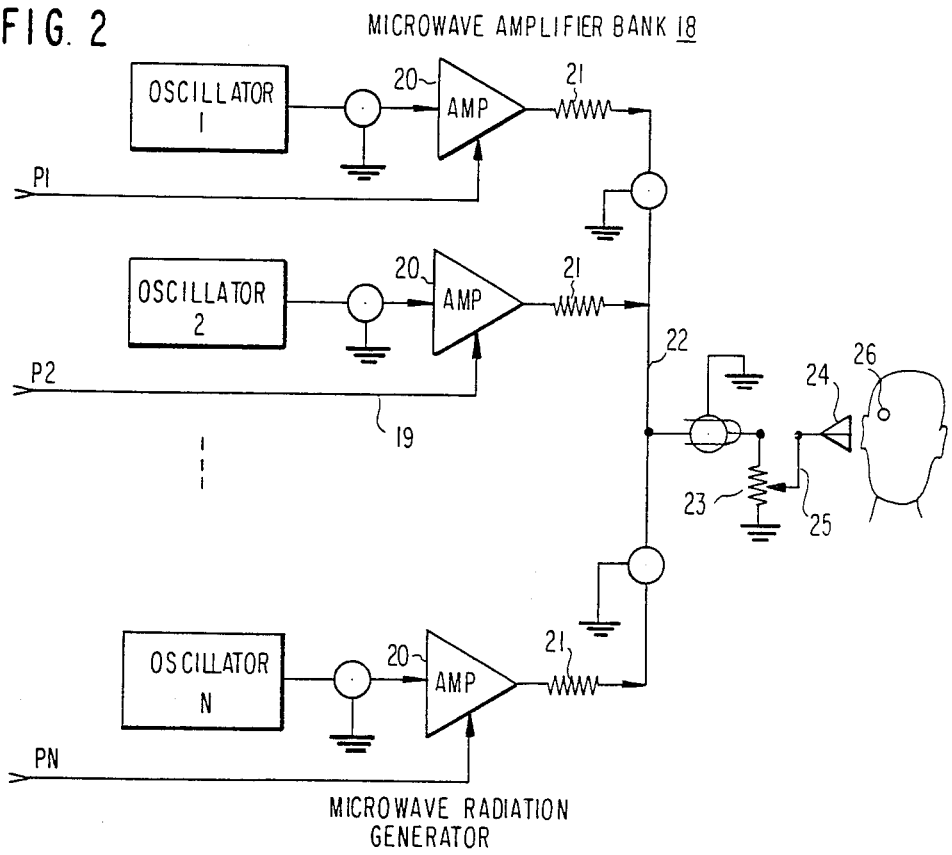
FIG. 2 shows the microwave generation and antenna portion of the hearing device of this invention.

Referring now to FIG. 1 and FIG. 2 there is shown an apparatus which provides for induced perception of sound into a mammalian brain. This hearing device includes a microphone 10 which receives sounds, an acoustic filter bank 12 which separates the signals from the microphone into component frequencies, and a mode control matrix 14 which generates the mode signals which are used to control the intensity of microwave radiations which are injected into the skull cavity in the region of the auditory cortex.

The acoustic filter bank 12 consists of a bank of acoustic filters F1 through Fk which span the audible acoustic spectrum. These filters may be built from standard resistance, inductance, and capacitance components in accordance with well established practice. In the preferred embodiment there are 24 filters which correspond to the observed critical bandwidths of the human ear. In this preferred embodiment a typical list of filter parameters is given by Table 1 below:

TABLE I

| Filter No. | Center Frequency (Hz) | Bandwidth (Hz) |
|---|---|---|
| 1 | 50 | less than 100 |
| 2 | 150 | 100 |
| 3 | 250 | 100 |
| 4 | 350 | 100 |
| 5 | 450 | 110 |
| 6 | 570 | 120 |
| 7 | 700 | 140 |
| 8 | 840 | 150 |
| 9 | 1,000 | 160 |
| 10 | 1,170 | 190 |
| 11 | 1,370 | 210 |
| 12 | 1,600 | 240 |
| 13 | 1,850 | 280 |
| 14 | 2,150 | 320 |
| 15 | 2,500 | 380 |
| 16 | 2,900 | 450 |
| 17 | 3,400 | 550 |
| 18 | 4,000 | 700 |
| 19 | 4,800 | 900 |
| 20 | 5,800 | 1,100 |
| 21 | 7,000 | 1,300 |
| 22 | 8,500 | 1,800 |
| 23 | 10,500 | 2,500 |
| 24 | 13,500 | 3,500 |

The rectifier outputs one through K are feed to K mode partition devices. The mode partitioning devices each have N outputs wherein N is the number of microwave oscillators used to generate the microwave radiation. The outputs 1 through N of each mode partition device is applied respectively to the inputs of each gain controlled amplifier of the microwave radiation generator. The function of the mode control matrix 14 is the control of the microwave amplifiers in the microwave amplifier bank 18. In the preferred embodiment thus will be 24 outputs and 24 microwave frequency oscillators.

Connected to each microwave amplifier gain control line is a mode simulation device 16 which receives weighted mode signals from the mode partition devices 14. Each mode simulation device consists of one through k lines and diodes 17 which are each connected to summing junction 19. The diodes 17 provide for isolation from one mode partition device to the next. The diodes 17 prevent signals from one mode partition device from returning to the other mode partition devices which are also connected to the same summing junction of the mode summation device 16. The diodes also serve a second function which is the rectification of the signals received from the acoustic filter bank by way of the mode partition devices. In this way each mode partition device output is rectified to produce a varying DC voltage with major frequency components of the order of 15 milliseconds or less. The voltage at the summation junction 19 is thus a slowly varying DC voltage.

The example mode partition devices are shown in greater detail in FIGS. 3, 4, and 5. The mode partition devices are merely resistance networks which produce 1 through N output voltages which are predetermined divisions of the input signal from the acoustic filter associated with the mode partition device. FIG. 3 shows a mode partitioning device wherein several outputs are associated with each series resistor 30. In the embodiment depicted in FIG. 4 there is an output associated with each series resistor only, and thus there are N series resistors, or the same number of series resistors as there are outputs. The values of the resistors in the mode partition resistor network are determined in accordance with the magnitudes of the frequency component from the acoustic filter bank 12 which is required at the summation point 19 or the gain control line for amplifiers 20.

The microwave amplifier bank 18 consists of a plurality of microwave oscillators 1 through N each of which is connected to an amplifier 20. Since the amplifiers 20 are gain controlled by the signals at summation junction 19, the magnitude of the microwave output is controlled by the mode control matrix outputs F1 through $F_n$. In the preferred embodiment there are 24 amplifiers.

The leads from the microwave oscillators 1 through N to the amplifiers 20 are shielded to prevent cross talk from one oscillator to the next, and to prevent stray signals from reaching the user of the hearing device. The output impedance of amplifiers 20 should be 1000 ohms and this is indicated by resistor 21. The outputs of amplifiers 20 are all connected to a summing junction 22. The summing junction 22 is connected to a summing impedance 23 which is approximately 50 ohms. The relatively high amplifier output impedance 21 as compared to the relatively low summing impedance 23 provides minimization of cross talk between the amplifiers. Since the amplitude of the microwave signal needed at the antenna 24 is relatively small, there is no need to match the antenna and summing junction impedances to the amplifier 20 output impedances. Efficiency of the amplifiers 20 is not critical.

Level control of the signal at antenna 24 is controlled by pick off 25 which is connected to the summing impedance 23. In this manner, the signal at antenna 24 can be varied from 0 (ground) to a value which is acceptable to the individual.

The antenna 24 is placed next to the subject's head and in the region of the subject's auditory cortex 26. By placement of the antenna 24 in the region of the auditory cortex 26, the microwave field which is generated simulates the microwave field which would be generated if the acoustic sounds were perceived with normal hearing and the auditory cortex was functioning normally.

Figure 2A:
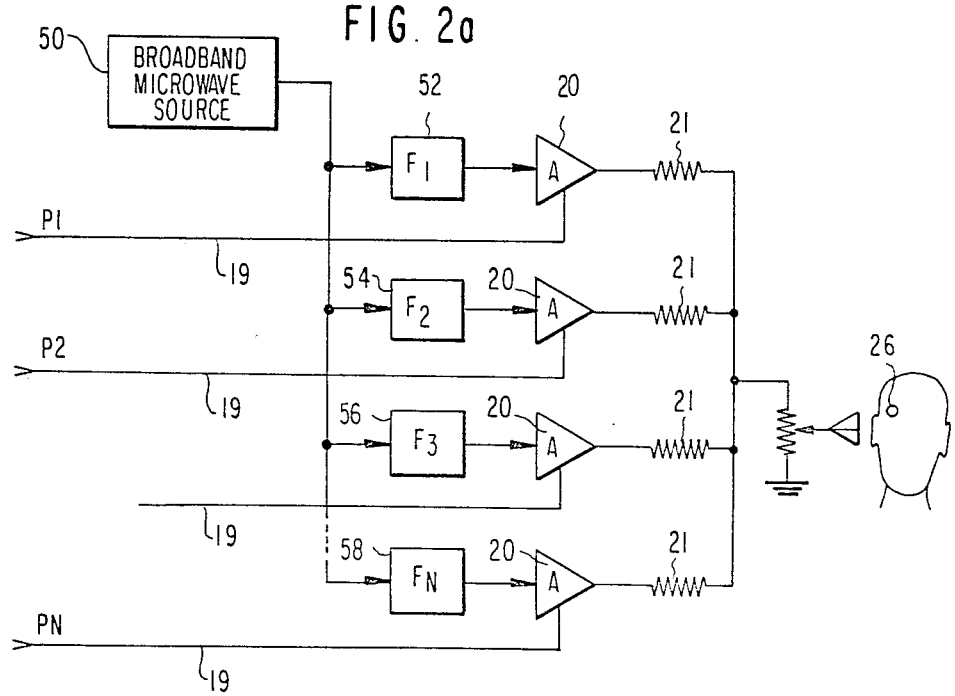

In FIG. 2A there is shown a second embodiment of the microwave radiation and generator portion of the hearing device. In this embodiment a broad band microwave source 50 generates microwave signals which are feed to filters 52 through 58 which select from the broad band radiation particular frequencies to be transmitted to the person. As in FIG. 2, the amplifiers 20 receive signals on lines 19 from the mode control matrix. The signals on lines 19 provide the gain control for amplifiers 20.

Figure 6:
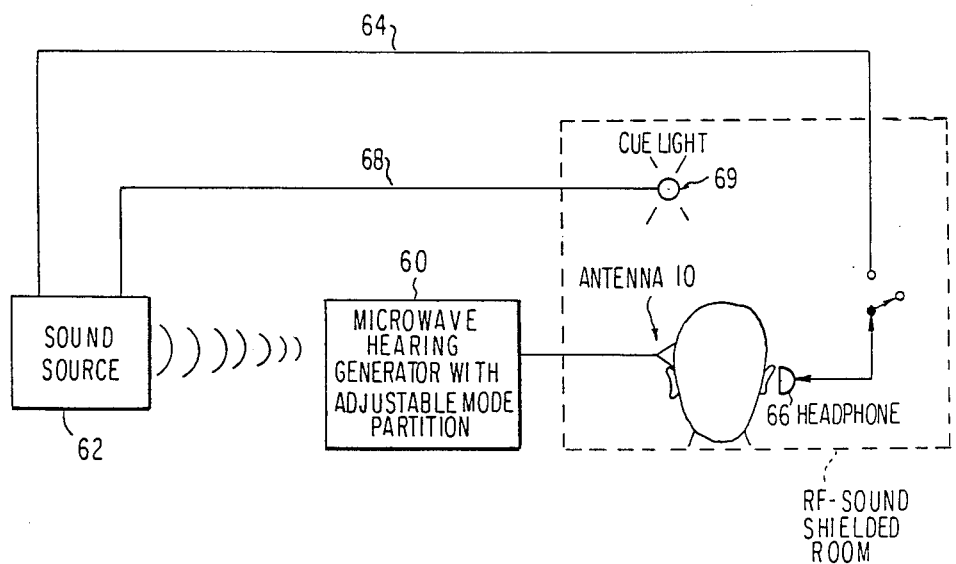
FIG. 6 shows a modified hearing device which includes adjustable mode partitioning, and which is used to provide initial calibration of the hearing device.

In FIG. 6 there is shown a modified microwave hearing generator 60 which includes a mode partition resistor divider network as depicted in FIG. 5. Each of the mode partition voltage divider networks in this embodiment are individually adjustable for all of the resistances in the resistance network. FIG. 5 depicts a voltage division system wherein adjustment of the voltage partition resistors is provided for.

In FIG. 6, the sound source 62 generates audible sounds which are received by the microphone of the microwave hearing generator 60. In accordance with the operation described with respect to FIGS. 1 and 2, microwave signals are generated at the antenna 10 in accordance with the redistribution provided by the mode control matrix as set forth in FIG. 5.

The sound source 62 also produces a signal on line 64 which is received by a head phone 66. The apparatus depicted in FIG. 6 is used to calibrate or fit a microwave hearing generator to a particular individual. Once the hearing generator is adjusted to the particular individual by adjustment of the variable resistors in the adjustable mode partition portion of the hearing generator, a second generator may be built using fixed value resistors in accordance with the adjusted values achieved in fitting the device to the particular subject. The sound produced by headphone 66 should be the same as a sound from the sound source 62 which is received by the microphone 10 in the microwave hearing generator 60. In this way, the subject can make comparisons between the perceived sound from the hearing generator 60, and the sound which is heard from headphone 66. Sound source 62 also produces a signal on 68 which is feed to cue light 69. Cue light 69 comes on whenever a sound is emitted from sound source 62 to the microwave generator 60. In this manner, if the subject hears nothing, he will still be informed that a sound has been omitted and hence that he is indeed perceiving no sound from the microwave hearing generator 60.

Figure 7:
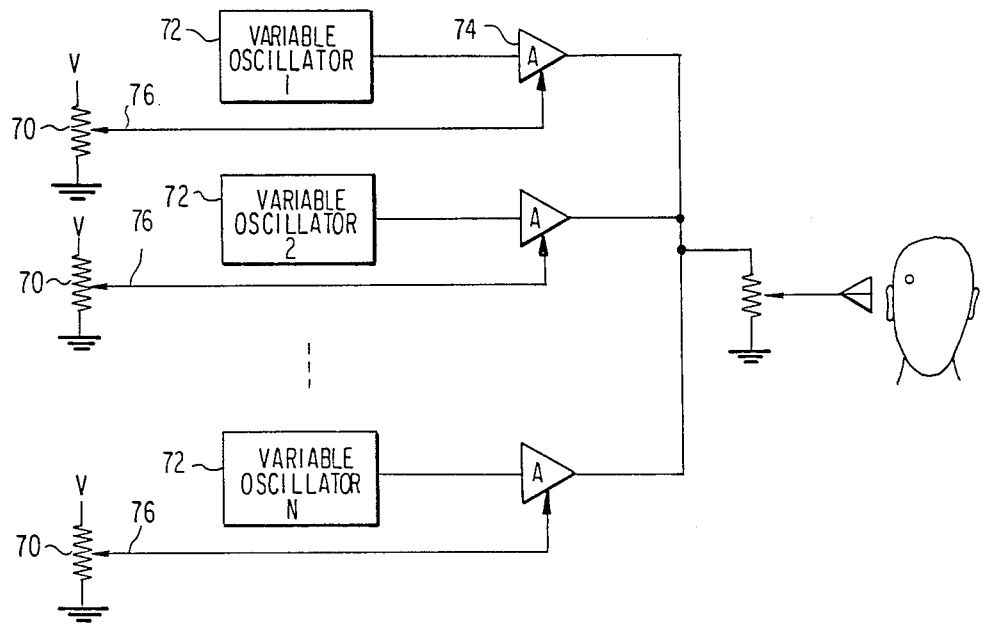
FIG. 7 shows a group of variable oscillators and variable gain controls which are used to determine hearing characteristics of a particular subject.

In FIG. 7 there is shown a modified microwave hearing generator which may be used to determine a subject's microwave mode frequencies. In this device, the acoustic filter bank and the mode control matrix have been removed and replaced by voltage level signal generated by potentiometers 70. Also included are a plurality of variable frequency oscillators 72 which feed microwave amplifiers 74 which are gain controlled from the signal generated by potentiometers 70 and pick off arm 76.

This modified microwave hearing generator is used to provide signals using one oscillator at a time. When an oscillator is turned on, the frequency is varied about the estimated value until a maximum acoustic perception by the subject is perceived. This perception however may consist of a buzzing or hissing sound rather than a tone because only one microwave frequency is being received. The first test of perception is to determine the subject's lowest modal frequency for audition (M=1). Once this modal frequency is obtained, the process is repeated for several higher modal frequencies and continued until no maximum acoustic perception occurs.

Another method of determination of a subject's modal frequencies is through anatomical estimation. This procedure is by measurement of the subject's cephalic index and the lateral dimensions of the skull. In this method, the shape is determined in prolate spheroidal coordinance.

Figure 8:
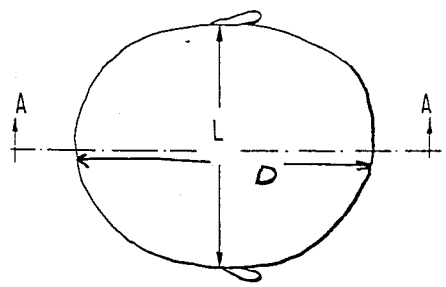
FIG. 8 shows a top view of a human skull showing the lateral dimension.
Figure 10:
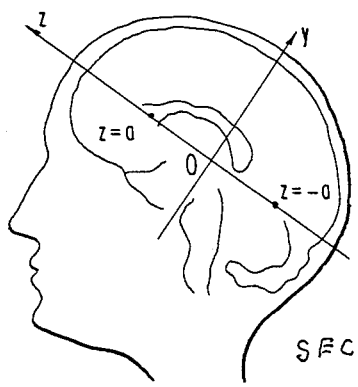
FIG. 10 shows a side view of a skull showing the medial plane of the head, section A—A.

Purely anatomical estimation of subject's modal frequencies is performed by first measuring the maximum lateral dimension (breadth) L FIG. 8, of the subject's head together with the maximum dimension D (anterior to posterior) in the medial plane of the subject's head. D is the distance along Z axis as shown in FIG. 10. The ratio L/D, called in anthropology the cephalic index, is monotonically related to the boundary value $\xi_o$ defining the ellipsoidal surface approximating the interface between the brain and the skull in the prolate spheroidal coordinate system. $\xi_o$ defines the shape of this interface; $\xi_o$ and D together give an estimate of a, the semi-focal distance of the defining ellipsoid. Using $\xi_o$ and a, together with known values of the conductivity and dielectric constants of brain tissue, those wavelengths are found for which the radial component of the electric field satisfies the boundary condition that it is zero at $\xi_o$.

These wavelengths are the wavelengths associated with the standing waves or modes; the corresponding frequencies are found by dividing the phase velocity of microwaves in brain tissue by each of the wavelengths.

A subject's microwave modal frequencies may also be determined by observing the effect of external microwave radiation upon the EEG. The frequency of the M equal 1 mode may then be used as a base point to estimate all other modal frequencies.

Figure 9:
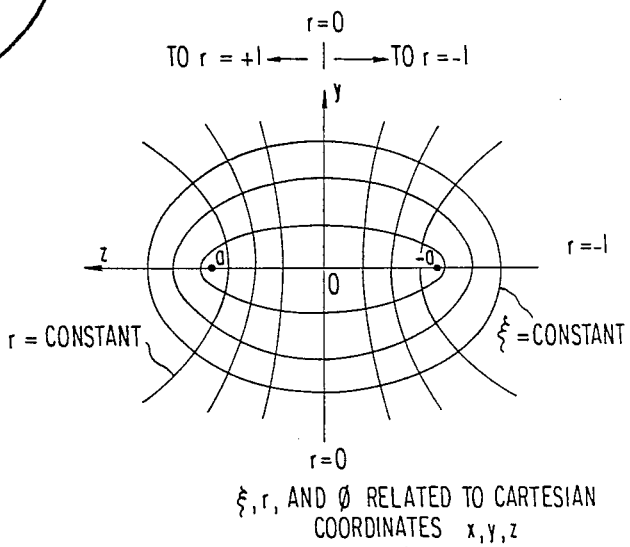
FIG. 9 shows the relationship of the prolate spherical coordinate system to the cartesian system.
Figure 11:
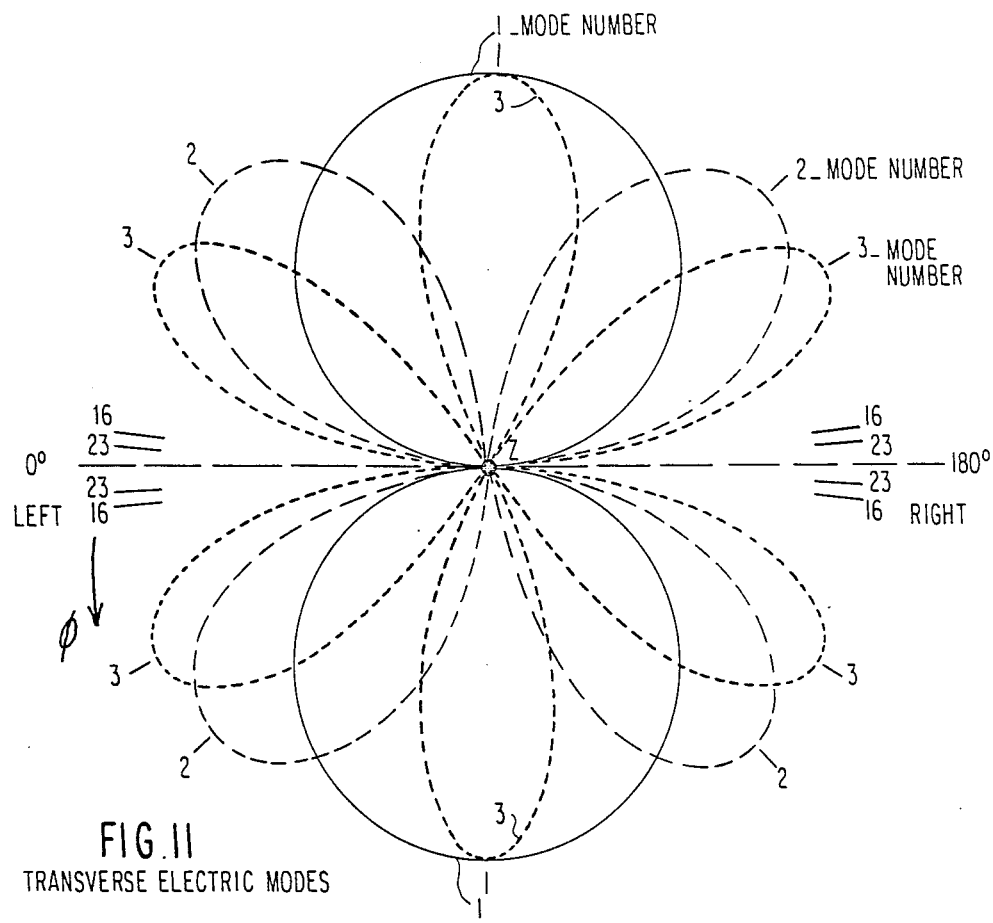
FIG. 11 shows a plot of the transverse electric field amplitude versus primary mode number M.

A typical example of such an estimation is where the subject is laterally irradiated with a monochromatic microwave field simultaneous with EEG measurement and the microwave frequency altered until a significant change occurs in the EEG, the lowest such frequency causing a significant EEG change is found. This is identified as the frequency of the M=1 mode, the lowest mode of importance in auditory perception. The purely anatomical estimation procedure (FIGS. 8, 9, 10) is then performed and the ratio of each modal frequency to the M=1 modal frequency obtained. These ratios together with the experimentally-determined M=1 frequency are then used to estimate the frequencies of the mode numbers higher than 1. The prolate spheroidal coordinate system is shown in FIG. 9. Along the lateral plane containing the x and y coordinates of FIG. 9, the prolate spheroidal coordinate variable $\phi$ (angle) lies FIGS. 9 and 10. Plots of the transverse electric field amplitude versus primary mode number m are shown in FIG. 11. The equation is $$E_{transverse}(m, \phi) = E_o \sin(m \phi)$$

Figure 12:
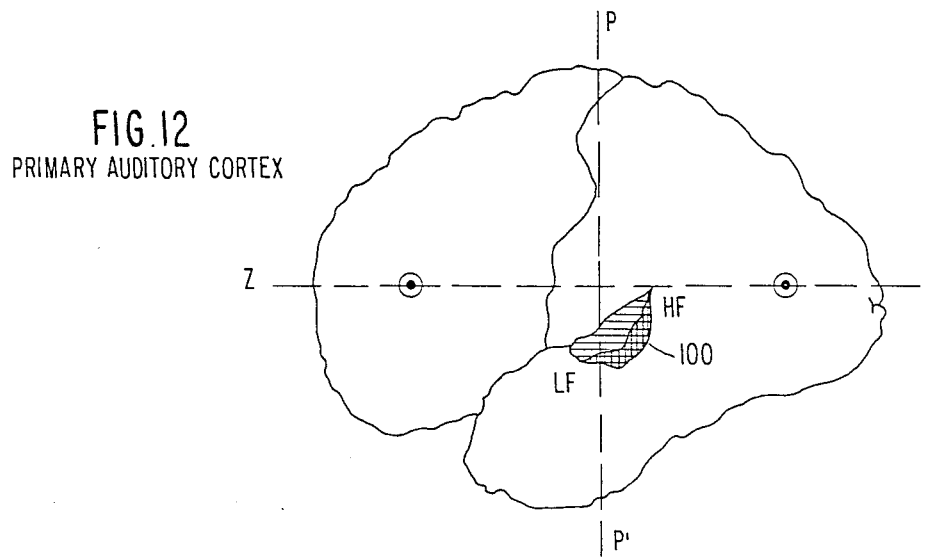
FIG. 12 shows a left side view of the brain and auditory cortex.

The "elevation view" FIG. 12, of the brain from the left side, shows the primary auditory cortex 10. The isotone lines and the high frequency region are toward the top of 100 and the low frequency region toward the bottom of 100.

The formula I, set forth below is the formula for combining modes from an iso-tone line at $\phi = \phi j$ being excited to obtain the total modal field at some other angular location $\phi$. For this formula, if we let $J = 1$ (just one iso-tone single frequency acoustic stimulus line), then it can be shown that ALL modes (in general) must be used for any ONE tone.

FORMULA I
RMS TRANSVERSE ELECTRIC
FIELD IN ANGULAR PLANE, $f(0)$ $$f(0) = \left[ \sum_{m=1}^{M} \left\{ \sin(m0) \cdot \sum_{j=1}^{J} e^{-(0-0j)/\Delta 0m} \sin(m0j) \right\}^2 \right]^{\frac{1}{2}}$$

$\phi$ = ANGLE (0° LATERAL)
$\phi_j$ = LOCATION OF j-TH SOURCE (TOTAL NUMBER J)
$\Delta\phi_m$ = ATTENUATION LENGTH (IN ANGLE) OF m-TH MODE
m = PRIMARY MODE NUMBER (HIGHEST MODE M)

Figure 13:
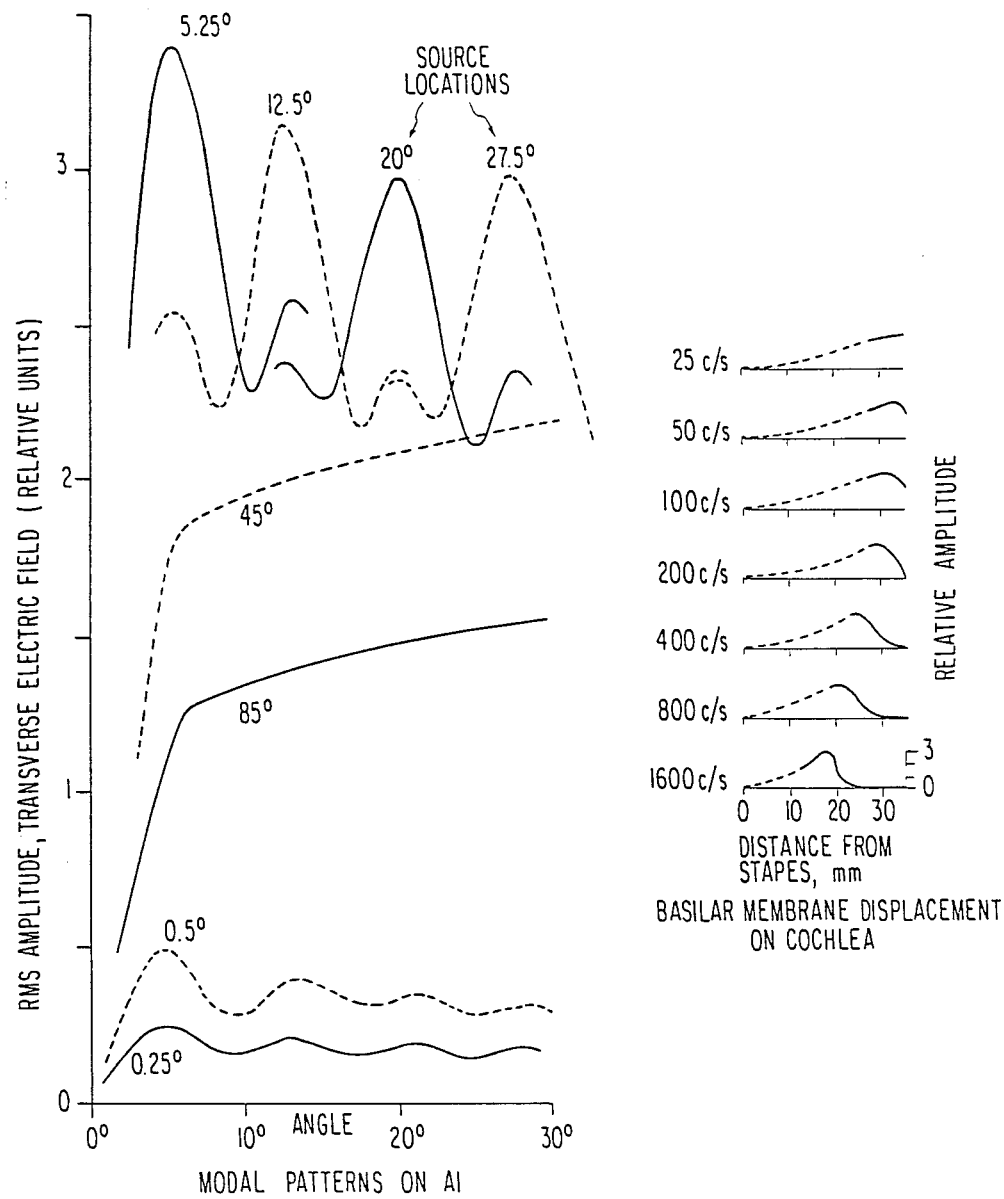
FIG. 13 shows the total modal field versus angle for source location.

FIG. 13 shows the resulting total modal field versus angle $\phi$ for source location $\phi$ at 5.25°, 12.5°, etc. With reference to the set of curves at the left top of this figure. A spacing of approximately 7.25° in $\phi$ corresponds to a tonal difference of about 1 octave. This conclusion is based on the side-lobes of pattern coming from $\phi = 5.25°$, etc. The total filed (value on y-axis) falls considerably below the top curves for source locations well below 5.25° (toward the high acoustic stimulus end) and also as the source of frequency goes well above 30° (low frequency end). $\phi$ is plotted positive downward from 0° at lateral location as indicates in FIG. 11.

Resistor weightings are obtained from the $|\sin(m[\phi - \phi j])|$, Formula I. The scale between acoustic frequency and $\phi$ must be set or estimated from experiment. Approximately 5.25 ± 1° corresponds to a tonal stimulus at about 2 kHz (the most sensitive region of the ear) since this source location gives the highest electric field amplitude.

The apparatus of FIG. 7 may also be used to determine values for a hearing device which are required for a particular subject. Once the modal frequencies have been estimated, the device of FIG. 7 which includes variable microwave oscillators may be used to determine values for the oscillators which match the subject, and to determine resistance values associated with the mode partition devices of the mode control matrix.

In FIG. 7 manual control of the amplifier gain is achieved by potentiometers 76. In this manner the amplifier gains are varied about the estimated settings for an acoustic tone stimulus in the region of two thousand Hertz (2 kHz) until maximum acoustic perception and a purest tone are achieved together. The term purest tone may also be described as the most pleasing acoustic perception by the subject. This process may be repeated at selected frequencies above and below 2 kHz. The selected frequencies correspond to regions of other acoustic filter center frequencies of the subject. When modal frequency (oscillator frequency) and gain set values (setting a potentiometer 76) are noted, it is then possible to calculate fixed oscillator frequencies and control resistor values for the adjusted hearing device for this particular subject.

In the event the subject has no prior acoustic experience, that is deaf from birth, estimated resistor values must be used. Also, a complex acoustic stimulation test including language articulation and pairs of harmonically related tones may be developed to maximize the match of the hearing device parameters for those of this particular subject.

Typical components for use in this invention include commercially available high fidelity microphones which have a range of 50 Hz to 15 kHz with plus or minus 3 dB variation.

The audio filters to be used with the acoustic filter bank 12 are constructed in a conventional manner, and have Q values of about 6. The filters may also be designed with 3 dB down points ($\frac{1}{2}$ the bandwidth away from the center frequency) occurring at adjacent center frequency locations.

The diodes 17 in the mode control matrix which provide isolation between the mode partition circuits are commercially available diodes in the audio range.

The microwave oscillators 1 through N and the microwave amplifiers 20 are constructed with available microwave transistors which can be configured either as oscillators or amplifiers. Examples of the transistors are GaAsFET field effect transistors by Hewlitt Packard known as the HFET series or silicone bipolar transistors by Hewlitt Packard known as the HXTR series.

All the cable between the oscillators, the microwave amplifiers, and the antenna should be constructed with either single or double shielded coaxial cable.

The antenna 24 for directing microwave signals to the audio cortex 26 should be approximately the size of the auditory cortex. A typical size would be one and one half CM high and one half to one CM wide. The antenna as shown is located over the left auditory cortex, but the right may also be used. Since the characteristic impedance of the brain tissue at these microwave frequencies is close to 50 ohms, efficient transmission by commercially available standard 50 ohm coax is possible.

The invention has been described in reference to the preferred embodiments. It is, however, to be understood that other advantages, features, and embodiments may be within the scope of this invention as defined in the appended claims.

What is claimed is:

1. A sound perception device for providing induced perception of sound into a mammalian brain comprising in combination:
   means for generating microwave radiation which is representative of a sound to be perceived, said means for generating including means for generating a simultaneous plurality of microwave radiation frequencies and means for adjusting the amplitude of said microwave radiation frequencies in accordance with the sound to be perceived; and
   antenna means located in the region of the auditory cortex of said mammalian brain for transmitting said microwave energy into the auditory cortex region of said brain.

2. A hearing device for perception of sounds comprising in combination:
   means for generating a signal representative of sounds;
   means for analyzing said signal representative of said sounds having an output;
   means for generating a plurality of microwave signals having different frequencies having a input connected to said output of said means for analyzing said signals, having an output;
   means for applying said plurality of microwave signals to the head of a subject, and
   whereby the subject perceives sounds which are representative of said sounds.

3. The apparatus in accordance with claim 2 wherein said means for generating a signal is a microphone for detecting sound waves.

4. The apparatus in accordance with claim 2 wherein said means for applying said plurality of microwave signals is an antenna.

5. The apparatus in accordance with claim 4 wherein said antenna is placed in the region of the auditory cortex of the subject.

6. The apparatus in accordance with claim 2 wherein the subject is a human being.

7. The apparatus in accordance with claim 2 wherein said means for analyzing said signal comprises:
   an acoustic filter bank for dividing said sounds into a plurality of component frequencies; and
   a mode control matrix means for providing control signals which are weighted in accordance with said plurality of component frequencies, having an output connected to said means for generating a plurality of microwave signal inputs.

8. The apparatus in accordance with claim 7 wherein said acoustic filter bank includes a plurality of audio frequency filters.

9. The apparatus in accordance with claim 8 wherein said audio frequency filters provide a plurality of output frequencies having amplitudes which are a function of said signal representative of sounds.

10. The apparatus in accordance with claim 9 wherein said amplitudes are the weighted in accordance with transform function of the signal representative of sounds.

11. The apparatus in accordance with claim 7 wherein said mode control matrix device includes a voltage divider connected to each of said plurality of said audio frequency filters.

12. The apparatus in accordance with claim 11 wherein each of said voltage dividers has a plurality of outputs which are connected in circuit to said means for generating a plurality of microwave signals.

13. The apparatus in accordance with claim 2 wherein said means for generating a plurality of microwave signals comprises a plurality of microwave generators each having a different frequency and means for controlling the output amplitude of each of said generators.

14. The apparatus in accordance with claims 2 wherein said means for generating a plurality of microwave signals comprises a broad band microwave source and a plurality of filters.

15. The apparatus in accordance with claim 13 wherein said generators each comprise a microwave signal source and a gain controlled microwave amplifier.

16. The apparatus in accordance with claim 13 wherein said means for analyzing output is connected to said means for controlling microwave amplifier output amplitudes.

17. The apparatus in accordance with claim 13 wherein analyzing includes K audio frequency filters.

18. The apparatus in accordance with claim 17 wherein there are N microwave generators.

19. The apparatus in accordance with claim 18 including a mode partitioning means which provides N outputs for each of said K audio frequency filters.

20. The apparatus in accordance with claim 19 wherein said N amplifiers each have K inputs from said mode partitioning means.

21. The apparatus in accordance with claim 20 wherein said N amplifiers have K inputs less the mode partitioning means outputs which are so small that they may be omitted.

22. The apparatus in accordance with claim 20 wherein said mode partitioning output device outputs each include a diode connected to each microwave amplifier gain control to provide isolation between all outputs.

23. The apparatus in accordance with claim 20 wherein said K audio frequency filters are chosen to correspond to the critical bandwidths of the human ear.

24. The apparatus in accordance with claim 20 wherein said N microwave generators are each adjustable in frequency output.

25. The apparatus in accordance with claim 18 wherein the frequency of each N microwave generators is determined by anatomical estimation.

26. The apparatus in accordance with claim 18 wherein the frequency of the lowest frequency microwave generator is chosen by determination of the effect of external microwave generation on the EEG of the subject.

27. The apparatus in accordance with claim 18 wherein the frequency of each of said N microwave generators corresponds to the subject's microwave modal frequencies.

28. The apparatus in accordance with claim 27 wherein the subject's modal frequencies are determined by measurement of the subject's cephalic index and the lateral dimensions of the skull.

29. The apparatus in accordance with claim 28 wherein the subject's lowest modal frequency is determined by varying the frequency of the lowest frequency microwave generator about the estimated value until a maximum acoustic perception is obtained by the subject.

* * * * *